United States Patent
Beestman et al.

(12)

(10) Patent No.: US 6,355,675 B1
(45) Date of Patent: Mar. 12, 2002

(54) EMULSIFIABLE CONCENTRATE OF A WATER-INSOLUBLE FUNGICIDE

(75) Inventors: George B. Beestman, Wilmington, DE (US); Kolazi S. Narayanan, Wayne, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/855,866

(22) Filed: May 15, 2001

(51) Int. Cl.[7] .......................... A01N 43/16; A61K 31/35
(52) U.S. Cl. ......................................... 514/456; 514/532
(58) Field of Search ................................ 514/269, 532, 514/456

(56) References Cited

U.S. PATENT DOCUMENTS 5,464,627 A * 11/1995 Fu et al. ..................... 424/409
6,033,681 A * 3/2000 Narayanan et al. ......... 424/405

FOREIGN PATENT DOCUMENTS

WO          9806780      *   2/1998

* cited by examiner

*Primary Examiner*—Alton Pryor
(74) *Attorney, Agent, or Firm*—William J. Davis; Walter Katz; Marilyn J. Maue

(57) ABSTRACT

A clear emulsifiable concentrate of a water-insoluble fungicide, without nonylphenol ethoxylate, that can be diluted in water to produce an aqueous ready-to-use formulation free from crystal formation or decomposition.

4 Claims, No Drawings

EMULSIFIABLE CONCENTRATE OF A WATER-INSOLUBLE FUNGICIDE

BACKGROUND OF THE INVENTION

1. Field of the Invention

This invention relates to a delivery system for agriculturally active chemicals, and, more particularly, to an efficacious emulsifiable concentrate for delivering a water-insoluble fungicide at a high loading that can be diluted in water to create a ready-to-use formulation free from crystal formation or decomposition.

2. Description of the Prior Art

Agriculturally active chemicals are most preferably applied in the form of aqueous emulsions, solutions or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, emulsions concentrates, when highly diluted into water, will not retain the active chemical, resulting in crystal growth that will inhibit biological efficacy and plug spray nozzles. Similarly, with suspension concentrates, once diluted into water, crystal growth becomes a serious problem.

These disadvantages are especially critical when it is desired to produce a ready-to-use formulation that is highly diluted into water.

Strobilurins are a new and highly effective class of fungicides; however, their water solubility is often less than one ppm. Furthermore, they are susceptible to decomposition and crystal growth in aqueous formulations. One such strobilurin, CGA 279202, has a water solubility of only 0.6 ppm, and is susceptible both to crystal growth and to decomposition.

Related references in this field are: U.S. Pat. Nos. 5,597,574; 5,672,353; 5,731,264; 5,766,615; 5,834,400; 5,928,992; 6,024,972 and 6,033,681.

Accordingly, it is an object of this invention to provide an emulsion concentrate that is dilutable with water to provide ready-to-use aqueous emulsion formulations of water-insoluble fungicides such as strobilurin that are free from crystal formation and decomposition.

SUMMARY OF THE INVENTION

What is provided herein is a clear emulsifiable concentrate of a water-insoluble fungicide, e.g. strobilurin, without using nonylphenol ethoxylate, that can be diluted in water to produce an aqueous ready-to-use formulation free from crystal formation or decomposition. The composition consists essentially of, by weight:

(a) 0.5–25% of water-insoluble fungicide, e.g. strobilurin;

(b) 5–60% of a water-insoluble organic solvent, e.g. aromatic petroleum distillate;

(c) 5–60% of a water-insoluble, polar organic co-solvent, e.g. N-octyl pyrrolidone or propylene carbonate;

(d) 5–60% of an anionic emulsifier, e.g. calcium dodecyl benzene sulfonate;

(e) 0–30% of a free acid anionic emulsifier, e.g. dodecyl benzene sulfonic acid;

(f) 5–30% of a water-insoluble polymer with hydrophobic and hydrophilic groups, e.g. $C_{16}$–$C_{20}$ alkyl pyrrolidone polymer, or co-polymer of vinylpyrrolidone/vinylacetate.

A matrix composition of the emulsifiable concentrate, i.e. without fungicide, also is provided herein, as well as aqueous ready-to-use formulations, i.e. concentrate plus water.

DETAILED DESCRIPTION OF THE INVENTION

Component Trade Names

Agrimer AL-22 A pyrrolidone polymer containing 80% $C_{16}$ alkylation

Agrimer AL-25 A pyrrolidone polymer containing 50% $C_{16}$ alkylation

Agrimer AL-30 A pyrrolidone polymer containing 80% $C_{20}$ alkylation

Agrimer VA-3 A Co-polymer containing 30% vinyl pyrrolidone and 70% vinyl acetate Agrimer VA-5 A Co-polymer containing 50% vinyl pyrrolidone and 50% vinyl acetate AgsolEx BLO gamma-Butyrolactone solvent AgsolEX 1 N-methyl-2-pyrrolidone solvent AgsolEx 8 N-n-octyl-2-pyrrolidone Ca/H DDBSA 50% Dodecyl benzene sulfonic acid, Calcium:free acid 5:1 mixture in Aromatic 150 petroleum solvent CGA279202 Methoxyimino-{2-[3-(trifluoromethyl-phenyl)-ethylideneamino-oxymethyl]-phenyl}-acetic acid methyl ester Azoxystrobin Methyl(E)-2-2-6-(2-cyanophenoxy) pyrimidin-4-yloxyphenyl-3-methoxyacrylate Kresoxin-methyl Methyl(E)-methoxyimino-[alpha-(o-toluloxy)-o-tolyl]acetate Strobilurins are a class of well known and widely-used water-insoluble fungicides of which CGA 279202, Azoxystrobin, and Kresoxin-methyl are representative examples. In accordance with the invention, a clear, emulsifiable concentrate of such fungicides, free of nonylphenol ethoxylate, that was diluted in water to produce an aqueous ready-to-use formulation free from crystal growth or decomposition, was made with the following components, in parts by weight.

TABLE 1

EMULSIFIABLE CONCENTRATE OF THE INVENTION

| Component | Suitable | Preferred |
|---|---|---|
| (a) Strobilurin, a water-insoluble fungicide e.g. CGA 279202 | 0.5–25 | 1–15 |
| (b) Water-insoluble solvent e.g. Aromatic 150, Aromatic 200, Exxate, Xylenes | 5–60 | 10–40 |
| (c) Water-insoluble polar co-solvent e.g. Propylene carbonate, AgsoIEX8, | 5–60 | 10–50 |
| (d) Anionic emulsifier e.g. Ca-Dodecylbenzene sulfonic acid, alkoxylated tristyryl-phenyl phosphoric acid salts | 5–60 | 10–50 |
| (e) Anionic emulsifier free acid/pH buffer e.g. Dodecylbenzene sulfonic acid, alkoxylated tristyrylphenyl phosphoric acid | 0–30 | 1–25 |
| (f) Water-insoluble polymer e.g. Agrimer AL-22, Agrimer AL30, Agrimer VA-3 Agrimer VA-5 | 5–30 | 10–20 |

This concentrate was diluted in water to provide a formulation containing 10–500 ppm strobilurin which was a ready-to-use formulation free from crystal development or decomposition.

A matrix composition of the invention also was made which include components (b) through (f), i.e. without the active fungicide, which was added later, to provide the emulsifiable concentrate.

Preparation of Concentrate of Invention

1. General Procedure

The procedure used to prepare water-dilutable concentrates is described below. These concentrates were screened for use as ready-to-use (RTU) water base formulations containing about 75 ppm fungicide. The emulsion concentrates containing ingredients (a) through (f) were prepared by mixing the ingredients until the polymers were dissolved and a uniform solution was obtained. Then CGA 279202 strobilurin fungicide was added. The resulting uniform, non-separating emulsion concentrate containing strobilurin fungicide was diluted into distilled water to 75 parts fungicide per million parts of water (ppm). Highly diluted concentrates in water were ready-to-use (RTU) finished formulations. Each RTU aqueous dilution was sub-sampled and placed into accelerated aging at 50° C., and 0° C. for one month. After accelerated aging, a tiny spec of crystals was added to each RTU as seed crystals to cause crystal formation in any RTU formulation that might be unstable to crystal formation. Each RTU was analyzed by optical microscopy for the presence of crystals and by gas chromatography to test its chemical stability.

2. Required Ingredients (a) Active ingredients: Water insoluble fungicides preferably strobilurins.

Examples: CGA 279202, Azoxystrobin and Kresoxin-methyl and others. Concentration in the concentrate: 0.5–25%; preferred 1–15%. Use-dilution in water to 10–500 ppm, preferably 50–100 ppm.

(b) Water-insoluble solvent:

Examples: Aromatic petroleum distillate (Exxon 150, or Exxon 200), Hydrogenated alkyl naphthalene, aliphatic hydrocarbons with greater than $C_8$ fraction, vegetable oil concentration in the concentrate: 5–60%; preferred 10–50%.

(c) Water insoluble polar co-solvent:

Examples: N-alkyl pyrrolidone, preferably NOP (Agsol Ex 8), Propylene carbonate, Esters like Exxate (mixed alkyl acetate with $C_5$–$C_8$ alkyl, with C6 predominating), alkyl caproate. Concentration in the concentrate: 5–60%; preferred 10–40%.

(d) (e) Anionic emulsifier: Soluble in both oil and water.

Examples: Ca dodecyl benzene sulfonate, preferably partially neutralized with the acid form to render an optimum pH range for stability of the active ingredient in solution. [pH range-4.0–7.0]. Concentration in the concentrate: 5–60%; preferred 10–50%.

(f) Water-insoluble polymer:

Copolymer with hydrophobic and hydrophilic groups selected from the following: Hydrophobic groups: alkyl graft, vinyl acetate, alkyl vinyl ether (with>C2 alkyl)acrylic esters, maleic acid esters, and others.

Hydrophilic groups: vinyl pyrrolidone, vinyl imidazolidinone, vinyl imidazole, vinyl caprolactam, maleic acid/salts, acrylic acid/salts and others. Specific examples: Agrimer AL 25, Agrimer VA 5, and Agrimer VA3 (preferably water insoluble copolymers). Concentration in the concentrate: 5–30%; preferred 10–20%.

Optional Ingredients

Polar water soluble solvents, e.g. NMP (Agsol Ex 1), BLO, antifoams e.g. soda soap, silicone oil, rheology modifiers e.g. natural gums, microbial inhibitors e.g. Proxel GXL.

The following examples 1–7 illustrate the invention more fully.

| Ingredients | Function | Ex 1 | Ex 2 |
|---|---|---|---|
| CGA 279202 | Active ingredient | 0.5 | 0.5 |
| NOP (Agsol Ex 8) | Polar water insoluble cosolvent | 3.8 | 0 |
| Propylene carbonate | Polar water insoluble cosolvent | 0 | 2.85 |
| Aromatic petroleum distillate 150 (Exxon) | Nonpolar solvent | 2.85 | 1.425 |
| Agrimer AL 25 | Polymer with hydrophobic | 1.425 | 0 |
| Agrimer VA5 | and hydrophilic groups | 0 | 1.425 |
| CaH/DDBSA [50% (Ca dodecylbenzene sulfonate + Dodecylbenzene sulfonic acid (5:1) in Aromatic pet.distillate, Exxon 150] | Anionic emulsifier with adjusted pH | 1.425 | 3.8 |
| Total | | 10 | 10 |
| Results | | | |
| Uniform initial concentration | | Yes | Yes |
| Crystals in 75 ppm dilution after one week, ambient | | No | No |
| Crystals in 75 ppm dilution after one month, ambient | | No | No |
| Crystal after aging and seeding | | No | No |
| CGA 279202 chemical stability | | Yes | Yes |

| Ingredients | Function | Ex 3 | Ex 4 | Ex 5 | Ex 6 | Ex 7 |
|---|---|---|---|---|---|---|
| CGA 279202 | Active ingredient | | | | | |
| Azoxystrobin | | | 0.1 | | 0.1 | |
| Kresoxin-methyl | | 0.5 | | 0.1 | | 0.1 |
| NOP (Agsol Ex 8) | Polar water insoluble cosolvent | | | | 3.96 | 3.96 |
| Propylene carbonate | Polar water insoluble cosolvent | 1.425 | 1.485 | 1.485 | | |
| Aromatic petroleum distillate 150 (Exxon) | Nonpolar solvent | 2.85 | 2.97 | 2.97 | 2.97 | 2.97 |
| Agrimer AL 22 | | | | | | |
| Agrimer AL 25 | Polymer with hydrophobic | | | | 1.486 | 1.485 |
| Agrimer AL 30 | and hydrophilic groups | | | | | |
| Agrimer VA5 | | 1.425 | 1.485 | 1.485 | | |

| | | | | | |
|---|---|---|---|---|---|---|
| Agrimer VA 3 | | | | | | |
| CaH/DDBSA | Anionic emulsifier with adjusted pH | 3.8 | 3.96 | 3.96 | 1.485 | 1.485 |
| [50% (Ca dodecylbenzene sulfonate + Dodecylbenzene sulfonic acid (5:1) in Aromatic pet.distillate, Exxon 150] | | | | | | |
| Total | | 10 | 10 | 10 | 10 | 10 |
| Results | | | | | | |
| Uniform initial concentration | | Yes | Yes | Yes | Yes | Yes |
| Crystals in 75 ppm dilution after one week, ambient | | No | No | No | No | No |
| Crystals in 75 ppm dilution after one month, ambient | | No | No | No | No | No |
| Crystal after aging and seeding | | No | No | No | No | No |

General Comments
Compositions with Agsol Ex 8 ( NOP) as Cosolvent

A commercially viable emulsion concentrate that is dilutable in water to a 75 ppm RTU formulation, that is free from crystal formation and in which CGA 279202 was chemically stable has been achieved, using Agrimer AL-25 with Agsol Ex 8 as co-solvent. See Example 1.

Compositions without NOP

Compositions with water-insoluble Agrimer VA-5 and polar water-insoluble propylene carbonate and anionic emulsifiers were stable to crystal formation after accelerated aging and seeding. See Example 2.

Kresoxin-methyl at 5% (Example 3) forms an emulsion concentrate that can be diluted in distilled water to 75 ppm Kresoxin-methyl and is stable to crystal formation throughout accelerated aging and seeding.

Three different strobilurin fungicides: Azoxystrobin, Kresoxin-methyl, and CGA 279202 are stable to crystal formation in emulsion concentrates that are diluted to 75 ppm RTU formulations when the emulsion concentrates contain a water-insoluble solvent, water-insoluble polar co-solvent, water-insoluble polymer and anionic emulsifier. See Examples 4–7.

What is claimed is:

1. A clear emulsifiable concentrate of a water-insoluble strobilurin fungicide, free of nonylphenol ethoxylate, that can be diluted in water to produce an aqueous ready-to-use formulation free from crystal formation or decomposition, consisting essentially of, by weight:

(a) 0.5–25% of said strobilurin fungicide,
(b) 5–60% of a water-insoluble organic solvent,
(c) 5–60% of a water-insoluble, polar co-solvent,
(d) 5–60% of an anionic emulsifier,
(e) 0–30% of a free acid anionic emulsifier, and
(f) 5–30% of a water-insoluble polymer with hydrophobic and hydrophilic groups.

2. A ready-to-use formulation created by diluting the concentrate of claim 1 to 10–500 ppm strobilurin fungicide in water which is stable to crystal formation and decomposition.

3. A composition of claim 1 wherein (a) is 1–15%, (b) is 10–40%, (c) is 10–50%, (d) is 10–50%, (e) is 1–25% and (f) is 10–20%.

4. A composition according to claim 1 wherein (b) is an aromatic petroleum distillate,
(c) is N-octyl pyrrolidone or propylene carbonate,
(d) is calcium dodecylbenzene sulfonic acid or alkylated tristyryl phenyl phosphoric acid,
(e) is dodecylbenzene sulfonic acid, or alkoxylated tristyrylphenyl phosphoric acid, and
(f) is a pyrrolidone polymer containing 50–80% $C_{16}$ alkylation, a copolymer of 30–50% vinyl pyrrolidone and 50–70% vinyl acetate.

* * * * *